United States Patent [19]

Gill et al.

[11] Patent Number: 4,671,769

[45] Date of Patent: Jun. 9, 1987

[54] DENTAL WORKING MODEL MOULDS

[75] Inventors: Malcolm Gill, Holywell Green; Steven Hoyle, Brighouse, both of United Kingdom

[73] Assignee: Malcolm Gill Ltd., West Yorkshire, England

[21] Appl. No.: 776,858

[22] Filed: Sep. 18, 1985

[30] Foreign Application Priority Data

May 31, 1985 [GB] United Kingdom ............... 8513824

[51] Int. Cl.⁴ .......................................... A61C 11/00
[52] U.S. Cl. ................................................ 433/213
[58] Field of Search .............................. 433/34, 213

[56] References Cited

U.S. PATENT DOCUMENTS 3,367,028 2/1968 Apfel ..................................... 433/34
3,436,827 4/1969 Pew ....................................... 433/34

Primary Examiner—Robert Peshock
Attorney, Agent, or Firm—Fay, Sharpe, Beall, Fagan, Minnich & McKee

[57] ABSTRACT

A mould is provided for the making and holding of working models for the manufacture of false teeth. The mould has upwardly extending side walls 11, 12, 13 and 14 and means to retain moulded material within the mould. The retaining means comprises at least one retaining member such as a locking strap 16 which, in use, is passed through at least one side wall of the mould to project into the moulded material.

10 Claims, 6 Drawing Figures

DENTAL WORKING MODEL MOULDS

BACKGROUND OF THE INVENTION

The invention relates to a mould for the making and holding of working models for the manufacture of false teeth.

DESCRIPTION OF THE PRIOR ART

A number of such moulds are known and one example is disclosed in U.K. Pat. No. 1 502 646. A model of a set of false teeth can be formed in the mould by means of a known technique and the model is then cut up into individual teeth so that further work can be carried out on the models of the individual teeth. The mould has special location ribs so that the separate teeth can be re-assembled in the mould in their original positions.

In some circumstances it may be convenient to be able to retain the individual models of the teeth within the model and U.K. Pat. No. 1 502 646 discloses retention elements for this purpose. The retention elements clip around a flange at the upper end of the walls of the mould and extend partially over the material in the mould, thus retaining the material in the mould. However two separate interengaging retention elements are required and the mould has to be provided with the special retaining flange.

A further example of this type of mould is shown in U.K. Registered Design No. 1 004 079. The mould shown in this design can be used with a simple U-shaped or C-shaped cross-section clip which simply clips around the entire side wall of the mould. However once again two separate components are required, a right hand component for clipping round the right hand side of the tray and a left hand component for clipping round the left hand side of the tray.

Both the known forms of retaining device partially obscure the upper surface of the moulded material.

OBJECT OF THE INVENTION

It is the object of the invention to provide a form of retaining element which enables a single, unhanded, component to be used for each side of the tray, the component providing more secure retention of the moulded material, without obscuring any of the upper surface of the moulded material.

SUMMARY OF THE INVENTION

Accordingly our invention provides a mould for the making and holding of working models for the manufacture of false teeth, the mould having upwardly extending side walls and means to retain moulded material within the mould, the retaining means comprising at least one retaining member which, in use, is passed through at least one side wall of the mould to project into the moulded material.

The retaining member may comprise an elongate strap, for example of plastics material, the strap being provided with an elongate rib which is inserted through a slot in at least one side wall of the mould.

Where the mould has two side walls which meet at an angle, the strap may be formed with two separate projecting ribs, to pass through two spaced apart slots respectively, the two parts of the strap being interconnected by a hinge, for example of flexible plastics material.

The mould, which may be of a plastics material, may initially be manufactured without slots, but with appropriately positioned areas of reduced wall thickness, the/or each slot subsequently being formed by forcing a rib through the wall in the area of reduced thickness.

Further objects and advantages of the invention will become apparent from the following description of an embodiment of the invention, given by way of example.

DESCRIPTION OF THE EMBODIMENT

Figure 1:
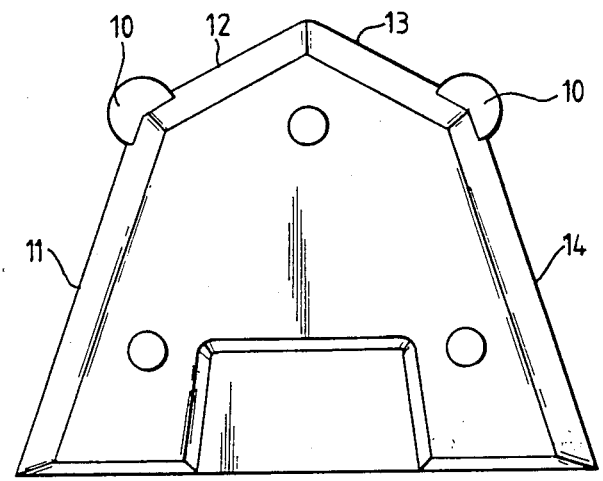
FIG. 1 is a base view of an embodiment of mould according to the invention.

The mould shown in the Figures is very similar to that shown in U.K. Registered Design No. 1 004 079 except that two lugs 10 are provided and each of four side walls 11, 12, 13 and 14 is provided, substantially midway up the wall, with an elongate area 15 of substantially reduced wall thickness.

The purpose of providing the lugs 10 is simply to provide an area of the mould which can be lightly tapped with a small hammer to free moulded material from the mould after the moulding process has been completed.

Provided in combination with the mould is a pair of locking straps indicated generally at 16.

Each strap comprises a longer portion and a shorter portion, corresponding in length to the areas of reduced wall thickness 15, the two portions being interconnected by a flexible hinge 17. Each portion comprises a base portion 18 from which a rib 19 projects.

Figure 2:
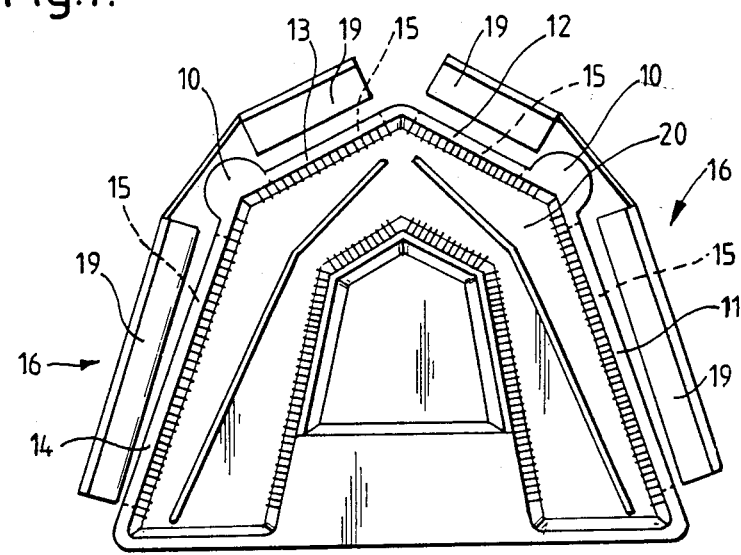
FIG. 2 is a plan view of the mould with two lock ready for placement.
Figure 3:
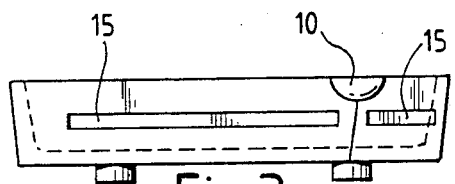
FIG. 3 is a side view of the mould.
Figure 4:
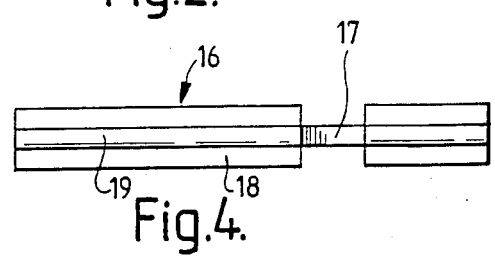
FIG. 4 is a side view of one of the locking straps.
Figure 5:
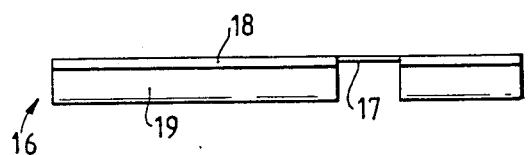
FIG. 5 is a plan view of the locking strap shown in FIG. 4.
Figure 6:
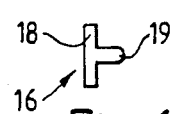
FIG. 6 is an end view of the locking strap shown in FIG. 4.

If the straps are positioned as shown in FIG. 2, each of the ribs 19 can be manually forced through one of the areas of reduced wall thickness 15 to form a slot. The dimensions of the ribs, in relation to the wall thickness, are such that the ribs will project into the mould area 20.

The mould is used as follows.

The locking straps are placed in position, with the ribs 19 projecting into the mould space 20. Material is then moulded within the mould and after the moulded material has hardened, the locking straps are removed and the lugs 10 are tapped to free the material from the mould. The material can then be cut up into any desired sections and when these sections are subsequently reassembled within the mould, they can be securely locked in position by reinserting the locking straps.

It will be seen that the locking straps are identical. In other words they are not handed and it is only necessary to manufacture one single component. Two of the components can then be used with each mould.

Because the locking straps engage with the interior of the moulded material and do not project over the upper end of the walls of a mould, none of the upper surface of the moulded material is obscured.

Because the ribs 19 effectively plug into the moulded material itself, they hold the moulded material much more securely than in known arrangements.

Because each of the walls 11, 12, 13 and 14 has its own retaining member, it is not necessary to release all of the reassembled moulded material if it is desired to work on only part of the reassembled material. For example if a user of the mould simply wishes to work on the material adjacent to the wall 13, it is only necessary to remove that part of the locking strap which engages in the slot of the wall 13 to remove the moulded material adjacent to the wall 13. The remainder of the moulded material remains securely in position.

The invention is not restricted to the details of the foregoing embodiment. For example the mould may be initially manufactured with the slots already present, instead of being manufactured with areas of reduced wall thickness.

Projecting tongues may be provided at one or both ends of each locking strap, for example by extending the base portion 18, to assist in removing the locking straps to free the moulded material.

Instead of using projecting ribs 19, other forms of projection may be used, for example pegs.

In some instances it may be convenient to separate the two parts of each locking strap by severing the hinge 17. Alternatively the two parts of the locking strap may be manufactured separately. Yet another possibility is to manufacture long stock lengths of the locking strap and cut off desired lengths of the locking strap as desired.

We claim:

1. A mould for the making and holding of working models for the manufacture of false teeth, the mould having base side walls extending upward from the base to form a moulding cavity for casting therein a model of a moulded material and retaining means to retain moulded material within the mould, the retaining means being separable from the side walls to facilitate removal of the model from the mould and comprising at least one retaining member which, in use, is moved relative to at least one side wall and thereby passed into and through the at least one side wall of the mould to project into the moulded material thereby prevent removal of the model from the mould.

2. A mould as claimed in claim 1, in which the retaining member comprises an elongate strap, the strap being provided with an elongate rib which is inserted through a slot in at least one side wall of the mould.

3. A mould as claimed in claim 2, having two side walls which meet at an angle, the strap being formed with two separate projecting ribs, to pass through the two spaced apart slots respectively, the two parts of the strap being interconnected by a hinge.

4. A mould for the making and holding of working models for the manufacture of false teeth, the mould having an end wall, two first side walls extending respectively from the two ends of said end wall, and two second side walls, each second side wall extending at an angle from an associated first side wall to meet the other second side wall, at least the inner face of each side wall being outwardly flared to facilitate removal of a model from the mould, at least one side wall being provided with upwardly extending ribs to facilitate location of a model within the mould, and each side wall having an elongate slot therein, and two locking straps separate from said side walls, one for each pair of side walls, each locking strap having a pair of ribs thereon, the ribs being shaped respectively to pass into and through the slots of the associated pair of side walls and hence project into the material of the model to releasably retain the model within the mould.

5. A method for the making and holding of working models for the manufacture of false teeth, comprising the steps of:

providing a mould having upwardly extending side walls and at least one retaining member separate from the side walls; and retaining molded material within the mold, by moving the retaining member relative to at least one side wall and simultaneously passing the retaining member into and through the at least one side wall of the mold to project into the molded material.

6. The method of claim 5, wherein said step of retaining includes passing a plurality of the retaining members through a plurality of the side walls to extend inwardly of the mold beyond the side walls and entirely below the upper surface of the side walls so that the portion of the retaining member extending within the mold completely extends within the molded material within the mold.

7. The method of claim 6, including the step of connecting all of said retaining members together with respective hinges during said step of retaining and passing.

8. The mold according to claim 1, wherein the portion of the retaining member that has passed through the side wall extends inwardly of the mold completely below the topmost surface of the side wall.

9. The mold according to claim 8, wherein there are a plurality of said retaining members respectively to pass through a plurality of said side walls when assembled in use; and said plurality of retaining members being movable relative to each other when assembled in use sufficiently so that at least one retaining member may be withdrawn from the interior of the mold without withdrawing the remaining retaining members.

10. The mold according to claim 9, wherein said side walls have weakened portions that are weakened sufficiently to be broken to produce an aperture when said retaining members are respectively passed through the side walls.

* * * * *